United States Patent [19]

Brill

[11] Patent Number: 5,738,430
[45] Date of Patent: Apr. 14, 1998

[54] METHOD AND APPARATUS FOR PREDICTING RETINAL ILLUMINANCE

[75] Inventor: Michael Henry Brill, Morrisville, Pa.

[73] Assignee: David Sarnoff Research Center, Inc., Princeton, N.J.

[21] Appl. No.: 693,725

[22] Filed: Aug. 7, 1996

Related U.S. Application Data

[60] Provisional application No. 60/014,274, Mar. 29, 1996.
[51] Int. Cl.[6] ................................................. G03B 21/14
[52] U.S. Cl. ............................................. 353/122; 348/78
[58] Field of Search ................................. 353/120, 122; 382/312, 321, 324; 348/78; 359/630

[56] References Cited

U.S. PATENT DOCUMENTS 3,533,684  10/1970  Stark et al. .................................. 348/78
3,551,052  12/1970  Reiber ........................................ 348/78

OTHER PUBLICATIONS

Starle, *Neurological Control Systems: Studies in Bioengineering*, Plenum, pp. 73–91 (1968).

Wyszecki, et al., *Color Science*, Wiley, pp. 105–106 (1982, 2nd ed.).

Trezona, "Luminance Level Conversions to Assist Lighting Engineers to use Fundamental Visual Data", Lighting Research & Technology, vol. 15, No. 2, pp. 83–88 (1983).

*Primary Examiner*—William Dowling
*Attorney, Agent, or Firm*—William J. Burke

[57] ABSTRACT

A method and apparatus for predicting how any given spatio-temporal light distribution would change an observer's pupil diameter. The method generates the instantaneous effect of luminance driving the pupil diameter, the cumulative driving function of the pupil diameter, and the evolving pupil diameter. Using the evolving pupil diameter together with the input luminance, the method computes the retinal illuminance distribution for the given input illuminance. The method is implemented as a software routine executed by a general purpose computer.

10 Claims, 2 Drawing Sheets

METHOD AND APPARATUS FOR PREDICTING RETINAL ILLUMINANCE

This application claims the benefit of United States Provisional Application No. 60/014,274 filed Mar. 29, 1996.

The invention relates to image compression systems and, more particularly, to a method and apparatus for predicting retinal illuminance from luminance distributions for use in a quality-based image processing or compression system.

BACKGROUND OF THE DISCLOSURE

Image compression systems, such as those systems based upon the Moving Pictures Experts Group (MPEG) standards, are generally lossy in that the image quality of the decoded image is degraded as compared to the original input image to the system. The visual perception of image degradation due to lossy compression depends on retinal illuminance from light produced by the various pixels within the decoded image. At low enough retinal illuminance, for example, all artifacts within the decoded image become invisible. Because the retinal illuminance of a pixel is the product of a measured pixel luminance and the pupil area of the eye, the pupil diameter enters implicitly into any computations involving visual quality of a display. However, conventional compression systems do not compensate for retinal illuminance. Furthermore, compression systems that use an image quality metric to control the compression process generally utilize a fixed pupil diameter.

In existing compression systems that use image quality metrics, typically a fixed pupil diameter of approximately 2 mm is used to facilitate conversion from pixel luminance to retinal illuminance. However, the pupil diameter during image viewing can be as large as 8 or 9 mm. Hence, there is a possible error factor of 16 or more between the estimated and the actual retinal illuminances.

Therefore, there is a need in the art for a method and apparatus that predicts retinal illuminance from luminance distributions for use in quality-based image processing and compression systems.

SUMMARY OF THE INVENTION

The method and apparatus of the present invention predicts how any given spatio-temporal light distribution would change an observer's pupil diameter. For use with a quality-based image processing or compression system, the light distribution is a pixel luminance distribution for an image or image sequence as portrayed upon a display screen, e.g., video monitor. The method of the present invention computes the instantaneous effect of luminance driving the pupil diameter, the cumulative driving function of the pupil diameter, and the evolving pupil diameter using a modified Trezona formula. Using the evolving pupil diameter together with the image luminance distribution, the method computes the retinal illuminance for the given input luminance distribution. Thus, for a given image, the invention predicts the light distribution upon an observer's retina.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
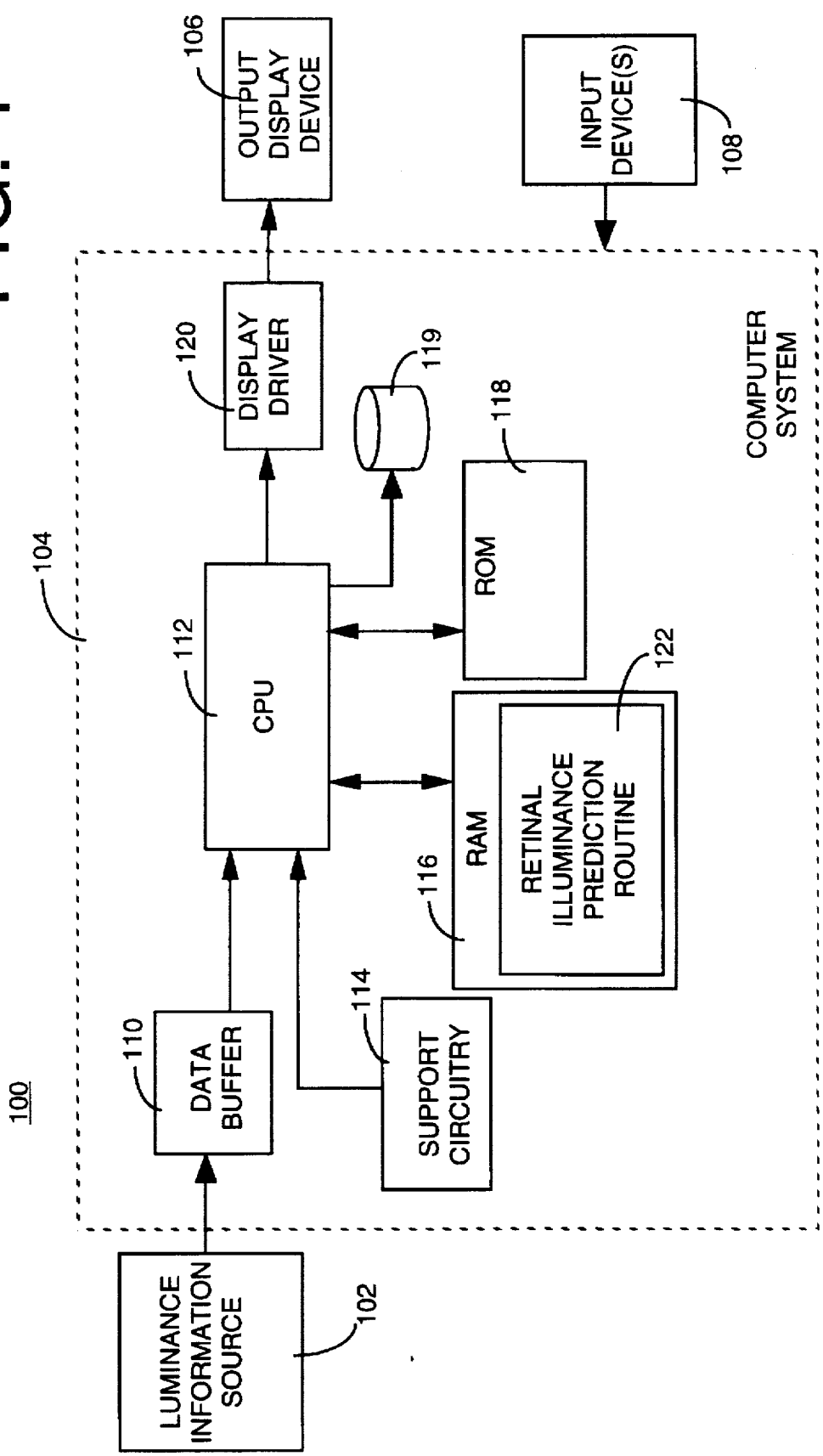
FIG. 1 depicts a block diagram of a general purpose computer that is programmed to execute the method of the present invention.

FIG. 1 depicts a block diagram of a general purpose computer system that, when executing a retinal illuminance prediction routine in accordance with the present invention, becomes a retinal illuminance prediction system 100 operating in accordance with the inventive method. The system contains a luminance information source 102, a computer system 104, one or more output devices 106 and one or more input devices 108. The luminance information source 102 provides a luminance distribution for each video frame in a video sequence, i.e., a luminance distribution $L(x,y,t)$. This luminance information includes a luminance value for each pixel location $(x,y)$ within an image, i.e., the information is a spacial distribution within each image frame and a spatio-temporal distribution over a sequence of frames in a video image sequence. This luminance information is available via a look-up table containing digital pixel values used to drive a calibrated display monitor. Alternatively, the luminance information is directly measured as a general display monitor generates light from the pixels displayed on a display monitor. The measuring device produces an array of luminance values representing the luminance at particular locations on the display monitor's surface.

The general purpose computer 104 facilitates computation of the retinal illumination for a given luminance distribution. Specifically, the computer system contains a data buffer 110, a central processing unit (CPU) 112, support circuitry 114, random access memory (RAM) 116, read only memory (ROM) 118, and a display driver 120. Additionally, a user interacts with the system through one or more input devices 108 such as a keyboard, mouse, trackball, touchpad, and the like. Also, the computer system utilizing the inventive method displays information and various graphical interface displays on the output display device 106 such as a computer monitor. Alternatively, the computer system may also interact with other output display devices such as a printer to provide a hard copy of any display that appears on the computer monitor.

The data buffer 110 provides data rate equalization (frame buffering) between the luminance information source and the CPU. Typically, this buffer is a first-in, first-out (FIFO) buffer. Such buffers are typically used to provide a constant data rate to the CPU while providing flexibility in the data rates that can be generated by the luminance information source.

The CPU 112 is typically a general purpose processor such as a Power PC, Pentium, or some other generally available processor. Power PC is a registered trademark of International Business Machines, Armonk, N.Y. and Pentlure is a registered trademark of the Intel Corporation, Santa Clara, Calif. Since the software implementation of the present invention is not required to execute on any specific processor, the routines of the present invention can be executed on any type Of processor or combination of processors in a parallel processing computer environment. In addition, using a general purpose computer, the method for retinal illumination computation may be accomplished within an image processing system or a video compression circuit.

The CPU 112 operates in conjunction with various other circuits such as RAM 116, ROM 118 and support circuitry 114 such as co-processors, clock circuits, cache, power supplies and other well known circuits. The operation and interrelationship of various computer components is well known in the art and does not require further explanation. The display driver 120 may be a video card, printer, driver or other common driver software or hardware as required by the object devices 106.

The RAM 116 stores the software implementation of the present invention. Typically, the routines of the invention are stored in a mass storage device 119 and recalled into temporary storage in RAM 116 when executed by the CPU 112. The invention is implemented as the retinal illumination prediction routine 122.

Figure 2:
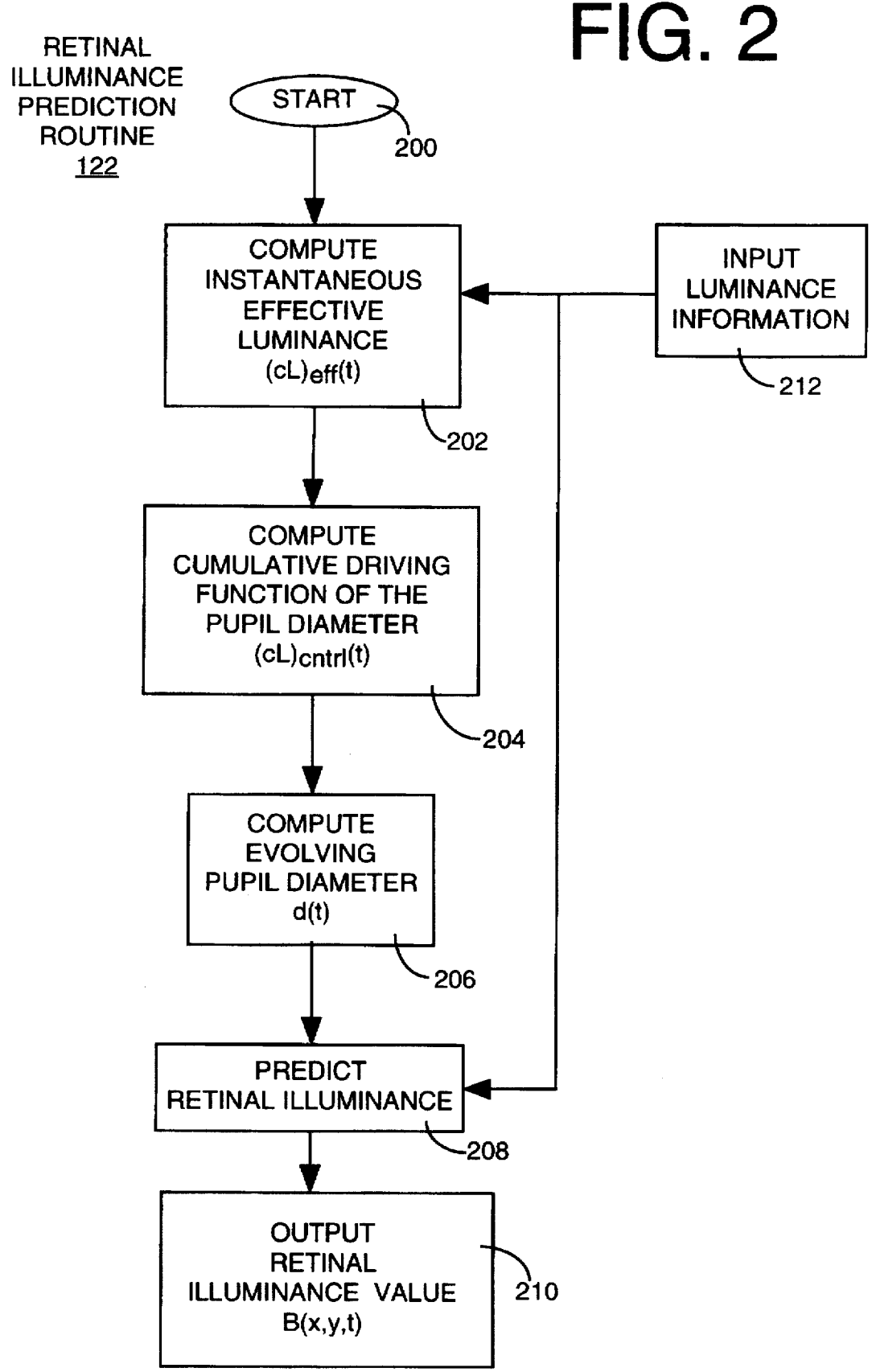
FIG. 2 depicts a flow diagram of the method of the present invention.

To compute the retinal illumination distribution B(x,y,t) in trolands given the luminance distribution L(x,y,t) in nits, the routine 122 is executed by the computer. FIG. 2 depicts a flow diagram of routine 122.

The routine begins at step 200 and proceeds to step 202, where the routine computes the instantaneous effective luminance $(cL)_{eff}(t)$ driving the pupil diameter of a virtual observer of a display producing a luminance distribution, using:

$$(cL)_{eff}(t) = 5.7037 \, D^{-3} \int dx dy L(x,y,t)(x^2+y^2)^{0.5}, \quad (1)$$

where D is the viewing distance from the virtual observer to an image and L(x,y,t) is the luminance of each pixel in the image as provided by step 212.

At step 204, the routine computes the cumulative driving function of the pupil diameter, $(cL)_{cntrl}(t)$ by using $$(cL)_{cntrl}(t) = \int dt' g(t-t')(cL)_{eff}(t'), \quad (2)$$

where g is the open-loop pupil-response function as substantially defined in L. Stark, "Neurological Control Systems: Studies in Bioengineering, Plenum, N.Y., 1968, pp.77–91. Therein, g(t) is defined as $$g(t) = 0.5c^{-3}(t-b)^2 e^{-(t-b)/c} u(t-b), \quad (3)$$

b=0.18 sec, c=0.1 sec, and u is the unit step function. In the case of static visual inputs (e.g., a time invariant image), $(cL)_{cntrl}$ automatically becomes $(cL)_{eff}$ because of the normalization of the transfer function g(t).

At step 206, the routine computes the evolving pupil diameter d(t) using a modified Trezona formula $$d(t) = 5 - 3 \tan h[0.4 \log_{10}\{(cL)_{cntrl}(t)\}], \quad (4)$$

The Trezona formula is disclosed in P.W. Trezona, "Luminance Level Conversions to Assist Lighting Engineers To Use Fundamental Visual Data", Lighting Research and Technology, 15, pp. 83–88 (1983).

Using the pupil diameter d(t) of Equation 4 and the luminance information L(x,y,t) provided by the luminance information source, the routine predicts, at step 208, the retinal illuminance B(x,y,t) using $$B(x,y,t) = L(x,y,t)\pi[d(t)/2]^2 \quad (5)$$

The result is a prediction of the retinal illuminance resulting from a given luminance distribution. The predicted value is made available at step 210 for various applications. The retinal illuminance value finds use in such applications as quality-based image processing and compression. In such systems, decoded image quality controls how the image is processed or compressed. The quality measure generally relies upon a retinal illumination parameter. One such system that uses a spatio-temporal "just noticeable differences"

quality model is disclosed in U.S. Pat. application Ser. No. 08/668,015, filed Jun. 17, 1996, and incorporated herein by reference. A quality-based compression system is disclosed in U.S. Pat. application Ser. No. 60/014,272, filed Mar. 29, 1996, and incorporated herein by reference.

To achieve a practical method for predicting retinal illumination for use in a quality-based image compression or processing system, the foregoing computations can be simplified to facilitate numerical analysis. As such, the integration is replaced with a summation over the image pixels, under the assumption that there is no appreciable luminance outside the image area. Also the geometric function, $(x^2+y^2)^{0.5}$ is computed prior to executing routine 122 in processing a complete sequence of image frames t, where t is quantized in units of one inter-frame interval. Since this function does not change with time (e.g., from frame to frame), the function is computed once for all x and y. Then the values are stored in memory for retrieval and use in processing each new image frame.

The convolution in step 204 involves computing $$(cL)_{cntrl}(t) = \int_0^\infty (cL)_{eff}(t-t')g(t')dt' \quad (6)$$

which is approximated by a summation of $(cL)_{cntrl}$ (j) using a time index j and a time step dt. The quantity dt is conveniently chosen as 1/30 of a second (the video frame rate) or 1/60 of a second (the video interlace-field rate).

The short duration g(t) requires modeling the time waveform q(t) of the frame as each frame turns on and off. To simplify the computation, the time required to excite a pixel and the time required for a pixel to cease emitting light is ignored, i.e., the emission period is approximated as a step function. The image sequence $(cL)_{eff}(t)$ is then represented as $$(cL)_{eff}(t) = \sum_{k=-\infty}^{\infty} I_D(k \cdot dt) q(t - k \cdot dt) \quad (7)$$

where $I_D$ and (k dt) are computed values of $(cL)_{eff}(t)$ at each frame time.

The function $(cL)_{cntrl}(t)$ can be sampled at any rate (including the frame rate) without loss of accuracy. If the function is time sampled at the rate $dt_1$, so that $t=j\,dt_1$, then $$(cL)_{cntrl}(j \cdot dt_1) = \sum_{k=-\infty}^{\infty} I_D(k \cdot dt) H(j \cdot dt_1 - k \cdot dt) \quad (8)$$

where $$H(\tau) = \int_0^\infty q(\tau - t') g(t') dt' \quad (9)$$

The integral represented by H is evaluated analytically assuming the function q is a simple rectangle function: q(t)=1 for 0<t<dt, else q(t)=0. This substitution leads to the following analytic expression for H $$H(\tau) = F(\max[0,\tau]) - F(\max[0,\tau-dt]) \quad (10)$$

where $$F(\tau') = -c[1 + ([\tau'-b]/c) + ([\tau'-b]/c)^2/2] e^{-(\tau'-b)/c} u(\tau'-b) \quad (11)$$

Lastly, the infinite limits of Equation 8 are replaced with finite limits imposed by the effective duration of H(τ). A conservative estimate for this duration is 0.5 seconds, which defines a summation limit N=0.5 sec/dt. Given this definition of N, and given that $\tau = j\,dt_1 - k\,dt$ (from Equations 8 and 9), it follows that the dummy index k in Equation 8 is constrained by $$j\, dt_1/dt - N < k < j\, dt_1/dt \quad (12)$$

From this constraint, Equation 8 reduces to the following finite-sum approximation:

$$(cL)_{cntrl}(j \cdot dt_1) = \sum_{cj-N}^{cj} I_D(k \cdot dt) H(j \cdot dt_1 - k \cdot dt) \quad (13)$$

where $N=0.5/dt$ and the lower and upper limits on the sum are respectively lowered and raised to the nearest integer value.

In sum, a digital implementation of the retinal illumination prediction routine uses Equation 10, 11, and 13. In order that all the required values of $I_D$ and $(k\, dt)$ are defined by Equation 13, the image sequence $I_D$ must extend N frames before the nominal starting point of the prediction, e.g., at $j=0$.

Those skilled in the art will recognize that the convolution of step 204 can be implemented using an FIR or IIR filter.

Although a single embodiment incorporating the teachings of the present invention has been shown and described in detail, those skilled in the art can readily devise many other varied embodiments that still incorporate these teachings.

What is claimed is:

1. A method for predicting retinal illuminance with regard to an image depicted on an image display comprising the steps of:
   generating an instantaneous effective luminance in response to luminance information representing luminance of each pixel in said video image;
   computing a cumulative driving function of pupil diameter in response to the instantaneous effective luminance;
   computing evolving pupil diameter in response to the cumulative driving function of pupil diameter; and
   predicting retinal illuminance from the luminance information and the evolving pupil diameter.

2. The method of claim 1, wherein said step of generating said instantaneous effective luminance further comprises the step of evaluating $$(cL)_{eff}(t) = 5.7037 D^{-3} \int dx\, dy\, L(x,y,t)(x^2+y^2)^{0.5}$$

where $(cL)_{eff}(t)$ is the instantaneous effective luminance, D is a viewing distance from a virtual observer to said image, x and y are pixel location coordinates for each pixel in said image, and $L(x,y,t)$ is a luminance value of each pixel.

3. The method of claim 1, wherein said step of computing said cumulative driving function of pupil diameter further comprises the step of evaluating $$(cL)_{cntrl}(t) = \int dt'\, g(t-t')(cL)_{eff}(t')$$

where $(cL)_{cntrl}(t)$ is the cumulative driving function of pupil diameter, $g(t)$ is an open-loop pupil-response function, and $(cL)_{eff}(t)$ the instantaneous effective luminance.

4. The method of claim 3, wherein said step of solving said cumulative driving function of pupil diameter further comprises the step of evaluating $$g(t) = 0.5 c^{-3}(t-b)^2\, e^{[-(t-b)/c]} u(t-b)$$

where b is 0.18 seconds, c is 0.1 seconds, and u is a unit step function.

5. The method of claim 1, wherein said step of computing said cumulative driving function of pupil diameter further comprises the step of evaluating $$(cL)_{cntrl}(j \cdot dt_1) = \sum_{cj-N}^{cj} I_D(k \cdot dt) H(j \cdot dt_1 - k \cdot dt)$$

where:

$(cL)_{cntrl}(j \cdot dt_1)$ is the cumulative driving function of pupil diameter for a sampling rate $dt_1$, $I_D$ is an image sequence;

$H(\tau) = F(\max[0,\tau]) - F(\max[0,\tau-dt])$;

$F(\tau') = -c([\tau'-b]/c) + ([\tau'-b]/c)^2/2)e^{(-[\tau'-b]/c)} u(\tau'-b)$;

N is 0.5 seconds/dt; $\tau$ is $(j\, dt_1 - k\, dt)$; and k is constrained by $(j\, dt_1/dt - N < k < j\, dt_1/dt)$.

6. The method of claim 1, wherein said step of computing evolving pupil diameter further comprises the step of evaluating $$d(t) = 5 - 3\tan h[0.4 \log_{10}\{(cL)_{cntrl}(t)\}]$$

where $d(t)$ is the evolving pupil diameter, and $(cL)_{cntrl}(t)$ is the cumulative driving function of pupil diameter.

7. The method of claim 1, wherein said step of computing retinal illuminance further comprises the step of evaluating $$B(x,y,t) = L(x,y,t) \pi [d(t)/2]^2$$

where $B(x,y,t)$ is the retinal illuminance, x and y are pixel location coordinates for each pixel in said video image, $L(x,y,t)$ is a luminance value of each pixel, and $d(t)$ is the evolving pupil diameter.

8. A method for predicting retinal illuminance with regard to a video image depicted on a video display comprising the steps of:

a) generating an instantaneous effective luminance in response to luminance information representing luminance of each pixel in said video image by evaluating $$(cL)_{eff}(t) = 5.7037 D^{-3} \int dx\, dy\, L(x,y,t)(x^2+y^2)^{0.5}$$

where $(cL)_{eff}(t)$ is the instantaneous effective luminance, D is a viewing distance from a virtual observer to said video image, x and y are pixel location coordinates for each pixel in said video image, and $L(x,y,t)$ is a luminance value of each pixel;

b) computing a cumulative driving function of pupil diameter in response to the instantaneous effective luminance by evaluating $$(cL)_{cntrl}(t) = \int dt'\, g(t-t')(cL)_{eff}(t')$$

where $(cL)_{cntrl}(t)$ is the cumulative driving function of pupil diameter, and $g(t)$ is an open-loop pupil-response function that is computed by evaluating $$g(t) = 0.5 c^{-3}(t-b)^2\, e^{[-(t-b)/c]} u(t-b)$$

where b is 0.18 seconds, c is 0.1 seconds, and u is a unit step function;

c) computing evolving pupil diameter in response to the cumulative driving function of pupil diameter by evaluating $$d(t) = 5 - 3\tan h[0.4 \log_{10}\{(cL)_{cntrl}(t)\}]$$

where $d(t)$ is the evolving pupil diameter; and d) predicting retinal illuminance from the luminance information and the evolving pupil diameter by evaluating $$B(x,y,t)=L(x,y,t)\pi[d(t)/2]^2$$

where $B(x,y,t)$ is the retinal illuminance.

9. A method for predicting retinal illuminance with regard to a video image depicted on a video display comprising the steps of:

a) generating an instantaneous effective luminance in response to luminance information representing luminance of each pixel in said video image by evaluating $$(cL)_{\mathit{eff}}(t)=5.7037 D^{-3}\int dx dy L(x,y,t)(x^2+y^2)^{0.5}$$

where $(cL)_{\mathit{eff}}(t)$ is the instantaneous effective luminance, D is a viewing distance from a virtual observer to said video image, x and y are pixel location coordinates for each pixel in said video image, and $L(x,y,t)$ is a luminance value of each pixel;

b) computing a cumulative driving function of pupil diameter in response to the instantaneous effective luminance by evaluating $$(cL)_{cntr}(j \cdot dt_1) = \sum_{cj-N}^{cj} I_D(k \cdot dt) H(j \cdot dt_1 - k \cdot dt)$$

where $(cL)_{cntr}(j \cdot dt_1)$ is the cumulative driving function of pupil diameter for a sampling rate $dt_1$, $I_D$ is an image sequence, where $$H(\tau)=F(\max[0,\tau])-F(\max[0,\tau-dt]),$$

$$F(\tau')=-c[1+([\tau'-b]/c)+([\tau'-b]/c)^2] e^{(-[\tau'-b]/c)} u(\tau'-b), \text{ and}$$

N is 0.5 seconds/dt, $\tau$ is $(j\ dt_1 - k dt)$, and k is constrained by $(j\ dt_1/dt - N < k < j\ dt_1/dt)$;

c) computing evolving pupil diameter in response to the cumulative driving function of pupil diameter by evaluating $$d(t)=5 -3 \tan h[0.4 \log_{10}\{(cL)_{cntr}(t)\}]$$

where $d(t)$ is the evolving pupil diameter, and $(cL)_{cntr}(t)$ is the cumulative driving function of pupil diameter; and d) predicting retinal illuminance from the luminance information and the evolving pupil diameter by evaluating $$B(x,y,t)=L(x,y,t)\pi[d(t)/2]^2$$

where $B(x,y,t)$ is the retinal illuminance.

10. Apparatus for predicting retinal illuminance with regard to an image depicted on an image display comprising:

means for generating an instantaneous effective luminance in response to luminance information representing luminance of each pixel in said video image;

means for computing a cumulative driving function of pupil diameter in response to the instantaneous effective luminance;

means computing evolving pupil diameter in response to the cumulative driving function of pupil diameter; and means for predicting retinal illuminance from the luminance information and the evolving pupil diameter.

* * * * *